United States Patent [19]

Mathiesen et al.

[11] Patent Number: 4,861,338
[45] Date of Patent: Aug. 29, 1989

[54] SAFETY SYRINGE

[75] Inventors: George E. Mathiesen, Inver Grove Heights; Charles H. Mayo, II, Marine on St. Croix, both of Minn.

[73] Assignee: Mediverse Inc., St. Paul, Minn.

[21] Appl. No.: 154,904

[22] Filed: Feb. 11, 1988

[51] Int. Cl.⁴ ............................................. A61M 5/00
[52] U.S. Cl. ................................ 604/110; 604/110; 604/188; 604/198; 604/263
[58] Field of Search ............... 604/110, 111, 181, 188, 604/197, 198, 211, 263, 185, 187, 192, 195, 212, 214, 216, 232, 234, 240–243; 128/762–767, 770

[56] References Cited

U.S. PATENT DOCUMENTS

| | | | |
|---|---|---|---|
| 3,890,971 | 6/1975 | Leeson et al. | 604/198 |
| 4,026,287 | 5/1977 | Haller | 604/195 |
| 4,391,272 | 7/1983 | Staempfli | 604/110 |
| 4,507,117 | 3/1985 | Vining et al. | 604/196 |
| 4,650,468 | 3/1987 | Jennings, Jr. | 604/194 |
| 4,675,005 | 6/1987 | De Luccia | 604/198 |
| 4,710,170 | 12/1982 | Haber et al. | 604/246 |
| 4,743,233 | 5/1988 | Schneider | 604/198 |
| 4,747,830 | 5/1988 | Gloyer et al. | 604/198 |
| 4,752,290 | 6/1988 | Schramm | 604/198 |
| 4,781,684 | 11/1988 | Trenner | 604/110 |

Primary Examiner—Max Hindenburg
Assistant Examiner—K. M. Reichle
Attorney, Agent, or Firm—Roger W. Jensen

[57] ABSTRACT

A disposable safety syringe having (i) a needle, and (ii) apparatus which, after use of the needle, permits the point of the needle to be withdrawn up into the syringe barrel to be shielded thereby to safeguard the user, i.e. to prevent accidental contact of the needle by an errant body part of the user, and (iii) additional apparatus for automatically locking the needle in the safe position to prevent reuse of the syringe.

18 Claims, 6 Drawing Sheets

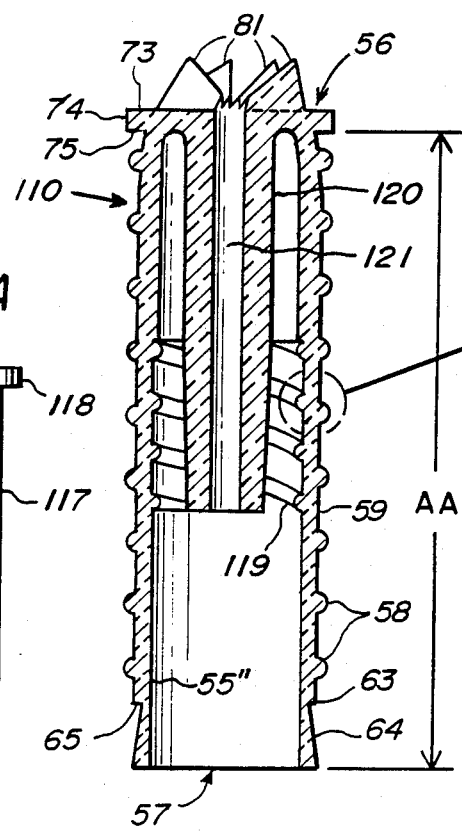
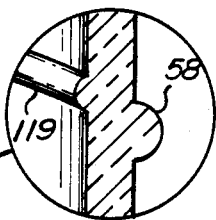
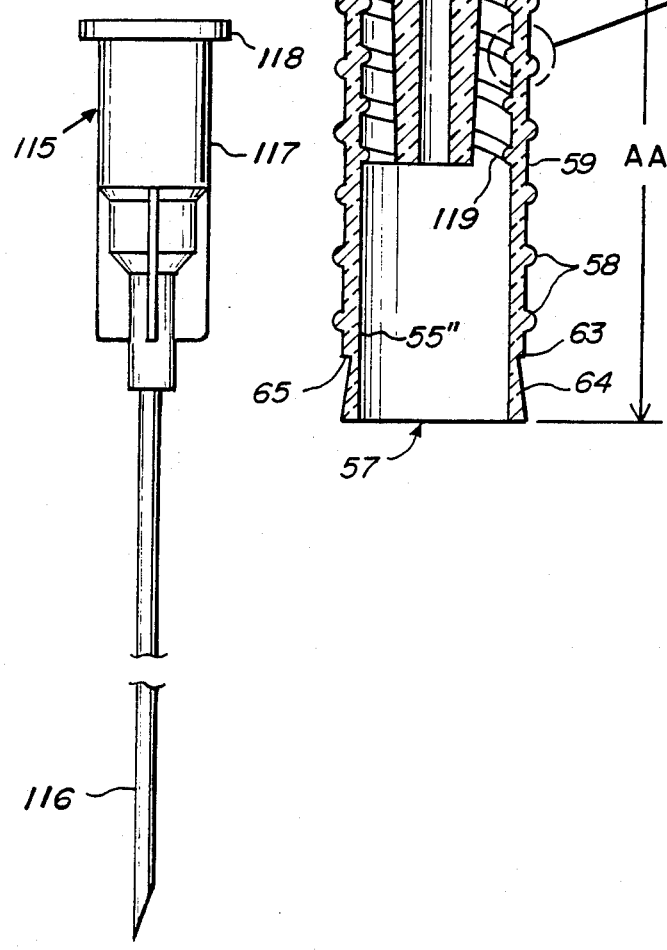
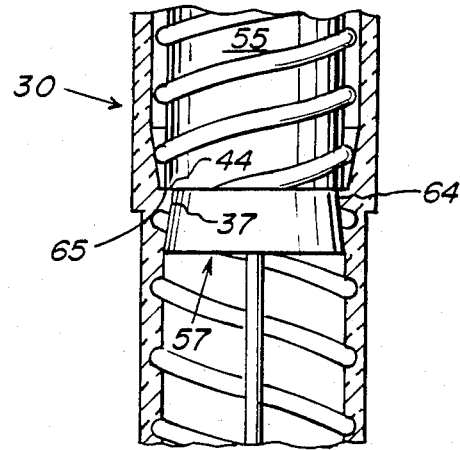

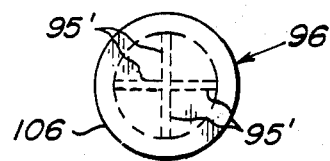
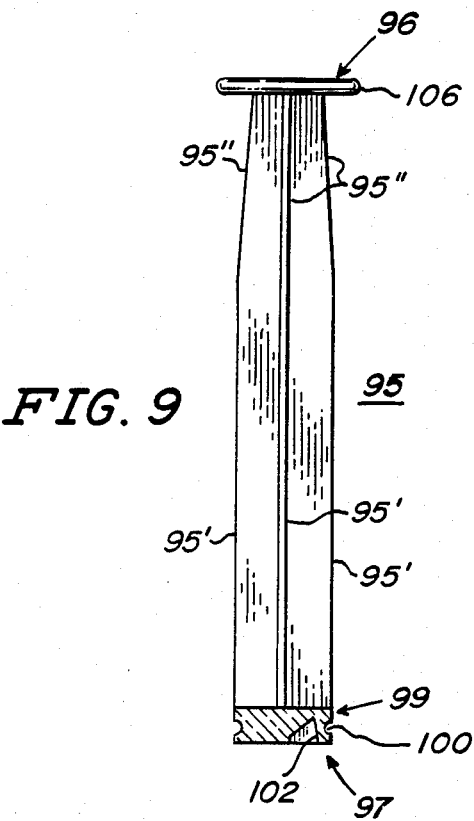
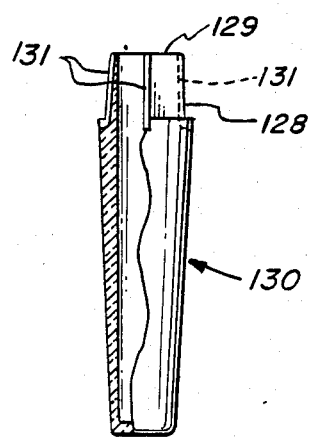
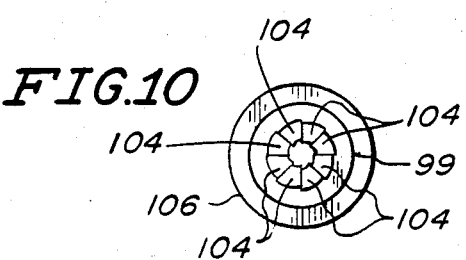
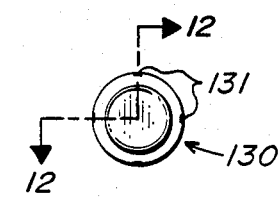

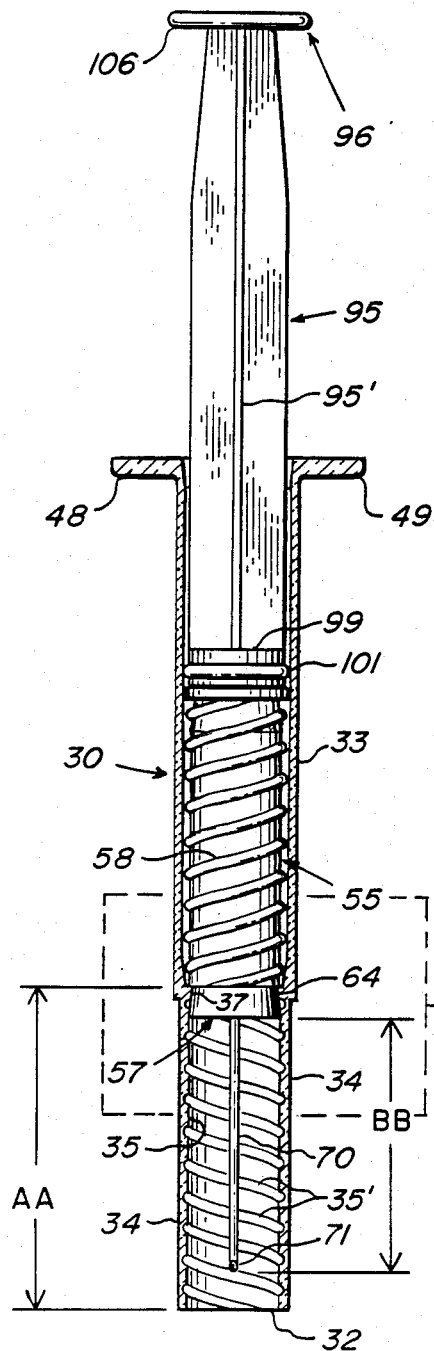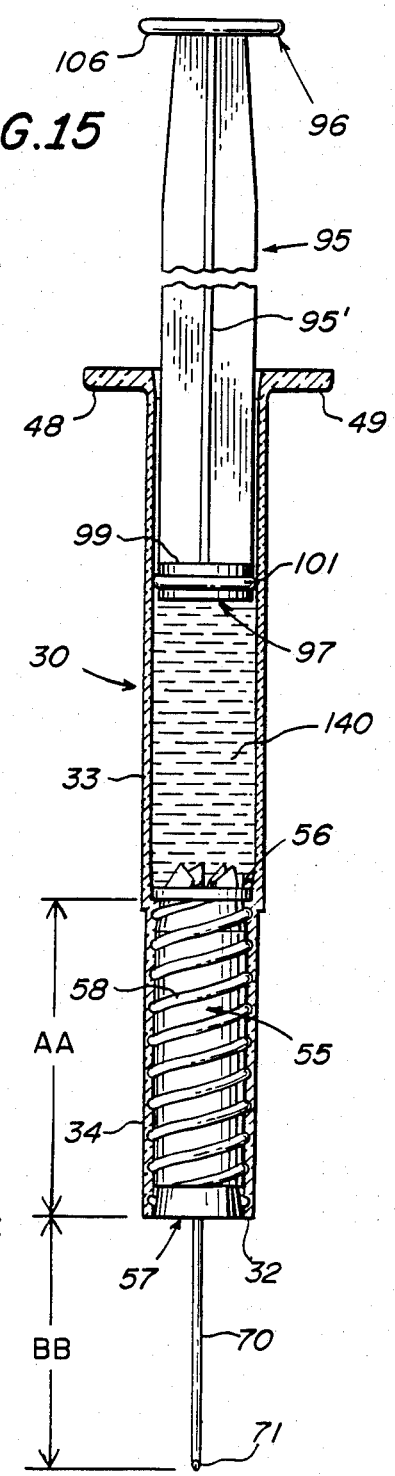

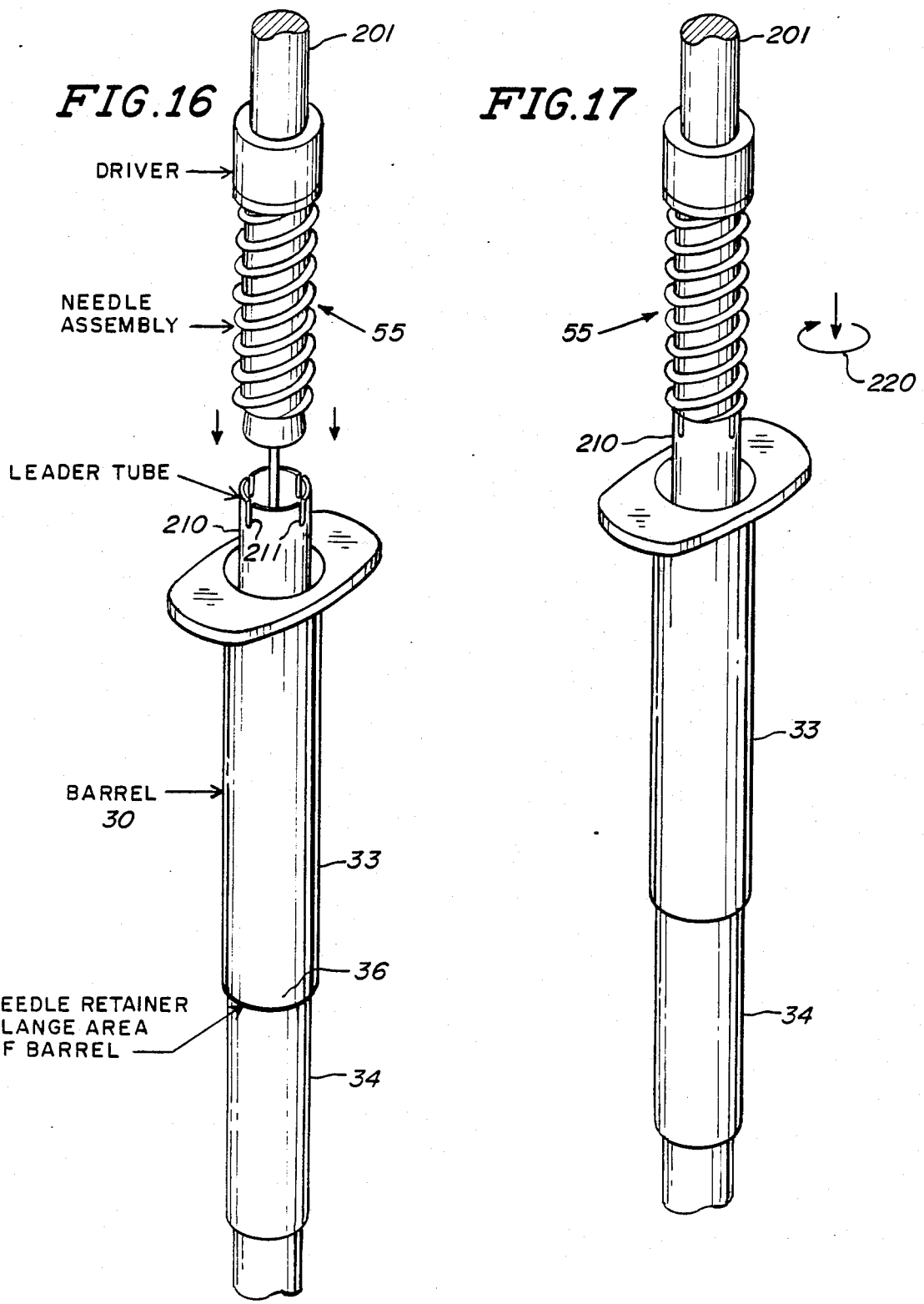

SAFETY SYRINGE

BACKGROUND OF THE INVENTION

AIDS and other serious infectious diseases have created an urgent need for a medical syringe which may be safely disposed or discarded following usage. There is an associated requirement, after such usage, for a simple means to permit a manual withdrawing of the needle up inside of the syringe barrel and locking same so as to provide two functions; the first is safety related, i.e. the point of the needle is withdrawn up within the syringe barrel so as to prevent an accidental sticking of medical staff or other personnel. The second function is to have the first safety means "unlockable" so as to prevent a used syringe from being used again, e.g. from surreptitiously being obtained by a drug addict for use thereby and possible sharing with other addicts.

There has been a general need for such a safety syringe for some time, as is evidenced by a number of prior art patents to be identified below. However, there has been a relatively recent increased awareness and understanding of AIDS, with the associated recognition that one of the principal ways of acquiring the AIDS related virus in one's body is via the "use" of a needle of an AIDS contaminated syringe. Such "use" may be intentional, such as drug addicts sharing needles. On the other hand, the "use" can be completely unintentional or accidental, e.g. medical staff personnel in a hospital emergency room being accidentally stuck by the needle of a syringe following use of the syringe on an accident victim who, after the fact, is determined to have the AIDS virus. An indication of the severity of the problem, with a special focus on the aforesaid drug addicts, is a January 1988 report by the New York Times which states, in part, that one out of every 61 babies born in New York City during December 1987 carried antibodies to the AIDS virus, indicating that their mothers were infected. The report further states that most infected women contract the human immunodeficiency virus or HIV, which is believed to cause AIDS, by sharing contaminated needles in drug abuse or by sexual intercourse with an infected male drug user.

In short, the above described problem is extremely serious. As is well known, the consequences of one accidentally acquiring AIDS are always profound and sometimes terminal.

A sampling of prior art, syringe patents which attempt to respond to the above identified need, but fall short in various ways, are U.S. Pat. Nos. 2,888,923 Reis; Lesson, et al, 3,890,971; Haller 4,026,287; Staempfli 4,391,272; Vining et al 4,507,117; Jennings, Jr. 4,650,468; and DeLuccia 4,675,005.

Using DeLuccia U.S. Pat. No. 4,675,005 as an example of a prior art syringe which falls short of the mark, a needle assemble is screwed into one threaded end of a syringe barrel assembly; in one embodiment a plunger means is arranged so as to transmit torque from the plunger to the needle assembly so as to screw the needle assembly out of threaded engagement with the barrel and then the plunger and attached needle assembly is moved axially all the way to the opposite end of the barrel at which point the plunger is rotated some additional revolutions so as to attach, through additional threaded means, the plunger to the barrel. The needle assembly follows with the plunger assembly and (as is shown in FIG. 4 of DeLuccia) the needle is totally brought inside the syringe barrel so as to provide safety. However, a threshhold problem of the DeLuccia syringe is that the plunger and needle assembly, after being withdrawn up into the barrel, as is shown in FIG. 4 thereof, is not truly locked. To the contrary, human desired to reuse the needle it is simply necessary to reverse the order of usage, namely, decoupling the plunger assembly from the end of the barrel following which the plunger and needle assembly may be moved axially so that the needle once again is projecting out through opening 42. The DeLuccia apparatus also is expensive to manufacture and complicated and time consuming to use, two important factors which rule against acceptance by professionals in the medical services field.

SUMMARY AND OBJECTS OF THE INVENTION

Simply stated, the predominent object of the present invention is to provide an improved disposable safety syringe. In the preferred embodiment the syringe has means which, after the syringe has been used in the normal way, provides for the needle to be withdrawn up into the syringe barrel and is permanently locked therein through an easily followed and quick procedure thus preventing accidental contact of the needle by a errant body part, and also preventing reuse of the syringe. This object can be summarized by stating that the invention provides a "no-stick" and non-reusable syringe.

Briefly, our safety syringe comprises a cylindrical hollow barrel member having top and bottom ends and axially abutting top and bottom tubular portions. The bottom tubular portion has an internally disposed female threaded section of a preselected axial length.

The invention further comprises a cylindrical axially extended needle holder means having (i) top and bottom axial ends, (ii) an externally disposed male threaded section of a preselected axial length and top and bottom axial ends and (iii) a central axially extending bore.

Elongated hollow needle means having a pointed end is positioned in the central bore of the needle holder means, the hollow needle means projecting a preselected axial extent beyond the bottom axial end of the needle holder means.

The assembled needle holder means and hollow needle means are positioned within the barrel member bottom portion with the male and female threaded sections in mutual mating and coacting engagement, and so that said pointed end of the needle means is projecting axially beyond the bottom end of the barrel member.

The invention further includes an elongated plunger means having, at a bottom end thereof, (i) integral piston means and (ii) torque transmitting tool means, said piston means and torque transmitting tool means being insertable into the top portion of the barrel member so that, upon axial movement of the plunger means down into the barrel, said piston and tool means are moved axially toward the top end of said needle holder means and, after a preselected amount of such axial movement, the tool means is engageable with said top axial end of said needle holder means which has means thereon for receiving said tool means and for receiving torque from said plunger means when the same is rotated. The transmission of rotational torque from the plunger means to the needle holder means (and the male threaded section thereon) causes rotation of the needle holder means with respect to said barrel member, more specifically with respect to the bottom tubular portion thereof (and said female threaded section thereon). Said relative rotation has the effect of simultaneously moving the needle holder means (and the needle) axially upwardly in said bottom tubular portion toward the top axial end of the female threaded section. After a sufficient rotation of the plunger (and hence the needle holder means) about its longitudinal axis, e.g. three turns, the male threads on the needle holder means will become disengaged from the female threaded section; the syringe is designed so that when such disengagement takes place, the point of the needle has been withdrawn axially up inside the bottom tubular portion of the barrel member by a sufficient amount so that accidental contact of the point of the needle by an errant body part is prevented.

The invention further provides a locking means for locking the needle holder means to the top end of the bottom tubular portion within said barrel member automatically upon said disengagement of the male threaded section from the female threaded section. Thus, once the needle holder means has been axially moved to the locked position, it is not possible to reuse the needle even though one might try by attempting to reverse the steps above set forth. The male and female threads are disengaged and the locking means prevents reengagement.

Thus, in the preferred embodiment the invention provides a "no stick" and nonreusable syringe, the nonreusable function being a function of the above described locking means.

A further object of the invention is to provide a unique "no-stick" syringe wherein after the syringe has been used, a means is provided for moving the needle assembly up into the barrel member of the syringe by sufficient axial amount so that accidental contact of the point of the needle by an errant body part is prevented.

Another object of the invention is to provide a unique means for locking the needle assembly to the barrel member so that relative axial movement therebetween is prevented.

Another optional feature and object of our invention is to have the hollow barrel member top and bottom tubular portions detachable from one another; this permits having a plurality of bottom tubular barrel portions of preselected, varied axial lengths to accommodate, respectively, a plurality of needle holder means of preselected, varied axial lengths.

BRIEF DESCRIPTION OF THE DRAWINGS

FIGS. 7 and 7A show, on an enlarged scale, an alternate needle holder means and detachable needle therefore and FIG. 8 shows a detail of the FIG. 7 holder;

FIGS. 9, 10 and 11 show respectively longitudinal, bottom and top views of an elongated plunger means, the plunger on the bottom of the apparatus in FIG. 9 being shown in section;

FIG. 12 is a view, partly in section, of a needle cap and FIG. 13 is an end view thereof, the apparatus shown in FIG. 12 in section being as viewed along section lines 12—12 of the apparatus shown in FIG. 13;

FIG. 14 shows an assembly of the hollow barrel member and the needle holder means including needle with the needle assembly means and needle having been moved axially up into (and safely within) the barrel member to a point where the aforesaid male and female threads have become disengaged and whereat the locking means holds the needle holder means against any further axial movement;

FIG. 14A is an enlarged showing of the locking means of FIG. 14;

FIG. 15 shows the assembly of FIG. 14 with the needle assembly in the lower or operational position and with fluid within the barrel, i.e. the syringe is shown ready for use;

FIGS. 16 and 17 show isometric views of one method of assembly of the needle holder assembly into the barrel member.

DETAILED DESCRIPTION OF THE PREFERRED EMBODIMENT OF THE INVENTION

Figure 1:
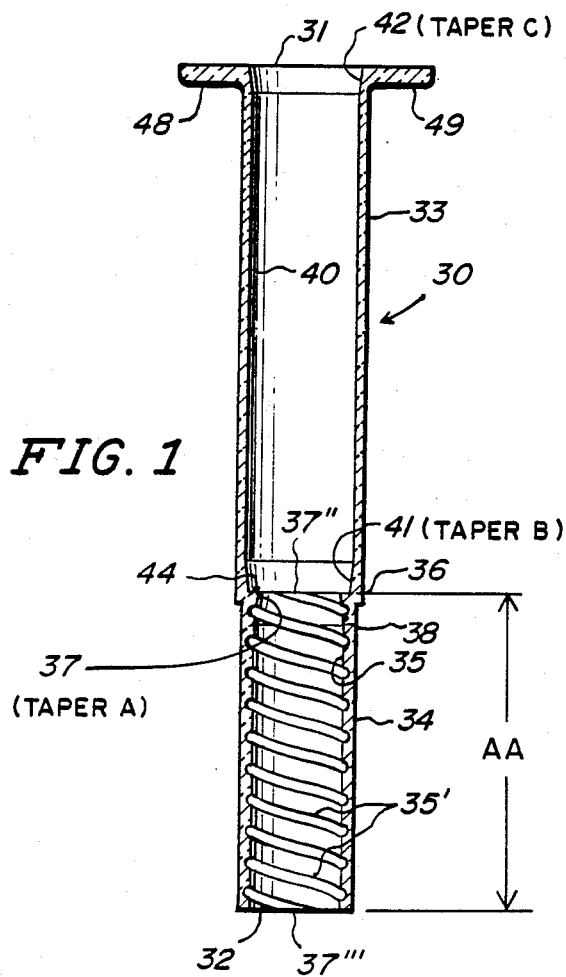

Referring to FIG. 1, the reference numeral 30 generally designates a cylindrical hollow barrel member of plastic o other suitable material having top and bottom ends 31 and 32 and axially abutting top and bottom tubular portions 33 and 34. Bottom tubular portion 34 has a bore 35 with internally disposed female threaded section 35' which has a preselected axial length; in this case the female threaded means 35' extends from the bottom end 32 of the barrel member axially upwardly to the junction between the axially abutting top and bottom tubular portions 33 and 34, the junction being identified in FIG. 1 by reference numeral 36. The axial length of threaded means 35' is identified by the reference AA in FIG. 1. As depicted threaded section 35' is a double thread but a single or other "multiple" thread could be used.

Figure 3:
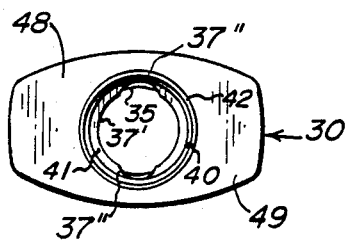
FIGS. 1, 2 and 3 show, respectively, cross-sectional longitudinal, and bottom and top views of a cylindrical hollow barrel member or syringe body member, FIG. 1 being a cross section of the entire body as viewed along section lines 1—1 of the apparatus shown in FIG. 2.
Figure 2:
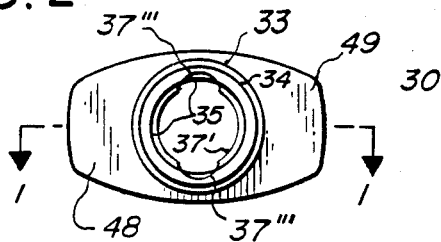

The inside diameter of the bottom tubular portion is constant until a short distance below the junction 36; beginning at this point (reference 38) the inside diameter of the bottom tubular portion is gradually reduced a suitable amount such as a ten degree (from vertical as shown) taper. The taper section per se is identified by reference numeral 37 and the angle of taper is identified in FIG. 1 by the designator "Taper A". The top end of taper portion 37 has a generally circular shape 37' depicted most clearly in FIGS. 2 and 3. FIG. 3 also shows a pair of lobes 37" on opposite sides of 37'; lobes 37" represent the upper termination of double threaded section 35'. FIG. 2 shows the lower or bottom termination of double threaded section 35, this termination is identified by two oppositely disposed lobes 37'''.

The top tubular portion 33 of barrel member 30 has a smooth internal bore 40 of generally constant inside diameter except at the extreme ends thereof. More specifically at the bottom of top tubular portion 33, adjacent to junction 36, the bore 40 has an inwardly extending taper 41 which is identified on the drawing as Taper B. Taper B may, in a typical case, be in the order of three degrees from vertical (as shown). Further, at the top of the bore 40 the inside diameter increases in an outwardly extending tapered section 42 (Taper C) to facilitate an easy insertion of the plunger assembly, to be described below. A representative and satisfactory taper for Taper C is approximately five degrees off of vertical (as shown).

It will be noted in FIG. 1 that the outside diameter of top tubular portion 33 is slightly greater than the outside diameter of the bottom tubular portion 34. In a syringe having a large capacity, the top tubular portion 33 could have a significantly larger external diameter than that of section 34.

Turning again to the junction 36, the reference numeral 44 has been used to designate a horizontal (as shown in FIG. 1) surface or shoulder defined between the top axial end of the tapered portion 37 and the bottom axial end of the tapered section 41 at the bottom of the upper tubular portion 33.

At the very top of, and integral with, top portion 33 of the barrel member (as shown in FIG. 1) are flanges 48 and 49 extending radially outwardly from the longitudinal axis of the barrel member 30; the function of flanges 48 and 49 being to facilitate the holding of the syringe in operation.

Figure 6:
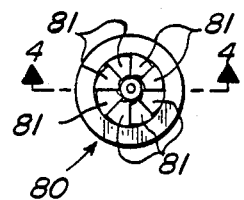
FIGS. 4, 5 and 6 show, respectively, cross-sectional longitudinal, bottom, and top views of a cylindrical axially extended needle holder means and having assembled therewith an elongated hollow needle means, FIG. 4 being a cross section of the assembled apparatus as viewed along section lines 4—4 of the apparatus shown in FIG. 6.
Figure 4:
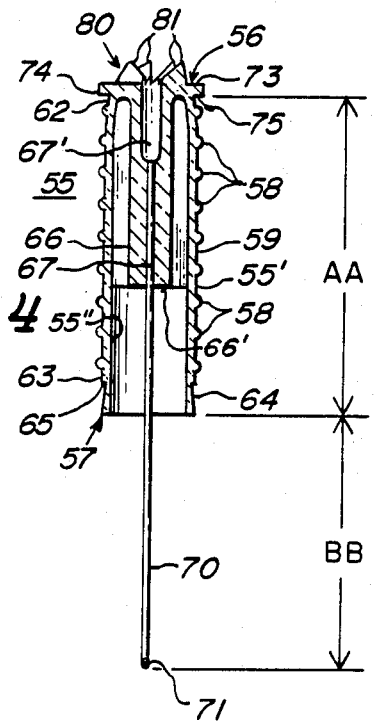
Figure 5:
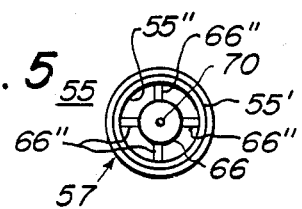

Referring to FIGS. 4, 5 and 6, a cylindrical axially extending needle holder means made from plastic or other suitable material is generally designated by the reference numeral 55 having top and bottom axial ends 56 and 57 and an externally disposed male threaded section 58, the outer diameter 55 of the needle holder means 55 being preselected and the threaded section 58 also being preselected so that the needle holder means may be screwed into the bottom tubular portion 34 of the barrel member 30 with said male and female threaded sections 58 and 35' being in mutual mating and coaxial engagement as shown in FIG. 15. As shown, the main body 55, is a hollow cylinder, the inner surface of which is identified by reference numeral 55''.

The male threaded section 58 has a preselected axial length or extent defining top and bottom axial ends thereof identified in FIG. 4 by reference numerals 62 and 63, respectively. Immediately below the bottom axial end 63, a circumferential tapered notch 64 is provided in the bottom end of the needle holder means, a horizontal (as shown in FIG. 4) shoulder 65 (see also FIG. 7) being defined between the bottom axial end 63 and the notched portion 64. The amount of taper for the portion 64 should generally be the same as that of Taper A for portion 37 in FIG. 1. The aforesaid preselected axial length of the male threaded section 58 is slightly less than dimension AA, the difference being the axial length of the tapered notch 64, as is clearly shown in FIGS. 4 and 7.

The needle holder means 55 further comprises a central hub 66, having therein a centrally located axially extending bore 67 in which is positioned, in fixed relationship, an elongated hollow needle means 70 having a pointed end 71. The pointed end 71 of the needle projects a preselected axial extent BB beyond the bottom axial end 57 of the needle holder means 55. The top end of bore 67 opens up into a bore 67', of a larger inside diameter, which extends to the top 56 of the needle holder assembly 55.

The hub 66 extends axially downwardly a preselected distance which can vary according to design choices; the bottom of hub 66 is identified by reference numeral 66'. Four ribs 66'' extend radially outward from hub 66 and are integrally connected to the main body 55' at the inner surface 55'' thereof.

Adjacent to the top end 56 of the needle holder means is a radially extending integral flange 73 having an outer circumferential surface 74 which is slightly greater in diameter than the outer diameter of male threaded portion 58; the diameter of flange 73 also being preselected so as to fit very snuggly against surface 41 at the bottom of portion 33 of the barrel. Furthermore, surface 74 has a slight taper off of vertical, as shown, so that when the needle assembly is assembled at the factory together with the barrel as shown in FIG. 15, the underside 75 of the flange 73 will fit tight against surface 44 of the barrel and the edge 74 of the circular flange 73 will be tight against the tapered surface 41 of the barrel thus assuring a fluid tight fit between the assembled barrel 30 and the needle assembly 55 so that, upon operation of the plunger assembly (to be described below), fluid will flow only down through bore 67' and the hollow needle means 70.

Also, at the very top axial end 56 of the needle holder means 55 is a tool receiving means 80 for receiving rotational torque, the tool receiving means comprising (see also FIG. 6) a plurality of beveled teeth members 81 arranged concentrically about the top of bore 67'.

In FIG. 9 is depicted an elongated plunger means 95 having a longitudinal axis and top and bottom ends 96 and 97. Plunger 95 is made from a plastic or other suitable material, except for its ends, a cruciform transverse cross section defining ribs 95' to provide a favorable strength to weight ratio. At the bottom end 97 is an integral piston means and torque transmitting tool means; more specifically, a piston 99 having a circular transverse cross section and a short axial extent is integral with the plunger means 95. Along the short axial extent thereof is a circumferential half-circle groove 100 for receiving an O-ring seal 101 (see FIG. 14). Further, the piston 99 has a downwardly axially facing cup-like recess 102 on the bottom axial face of which are arranged a plurality of beveled teeth 104 which are arranged in a circular configuration as best shown in FIG. 10 to thus constitute a torque transmitting tool means on the bottom axial face of the plunger assembly. The dimensions and tapers of the teeth 104 are preselected to mate mutually with the teeth 81 on the torque receiving means 80 at the top axial end 56 of the needle holder means 55.

At the top end of the plunger means 95, the rib elements 95' become progressively shorter, in a transverse sense, as designated by reference numerals 95'', At the very top 96 is a transverse end piece or knob 106 having a short axial extent and a significant radial extent (with a circular transverse cross section) so as to facilitate an efficient and comfortable means for the human operator to apply both axial movement to the plunger means 95 when the plunger assembly is being moved axially with respect to the barrel member 30; the end piece 106 of the plunger 95 further providing a convenient and efficient means for applying rotational torque to the plunger 95 when the torque transmitting tool means 104 at the bottom end thereof are engaged with the torque receiving means 81 on the top end of the needle holder means 55.

FIG. 7 shows an alternate needle holder means body identified by reference numeral 110. The scale of FIGS. 7 and 7A is twice that of FIGS. 1–6; nevertheless a comparison of FIGS. 7 and 4 will show substantially identical external features; thus, the same reference numerals are used for the same items. The main difference is that the FIG. 4 apparatus has the needle means 70 "fixed" to the needle holder means 55 by being positioned in the bore 67, all as aforesaid. The FIG. 7 version is intended to work in combination with a detachable needle means shown in FIG. 7A; this type of needle means is sold commercially by Becton Dickinson & Company of East Rutherford, New Jersey under the trademark "LUER-LOK". The needle apparatus shown in FIG. 7A is generally identified by reference numeral 115 comprising a hollow needle 116 connected at the top end thereof to an elongated hollow cylindrical plastic body 117 having an outwardly extending shoulder 118 at the very top thereof. The inner surface 55" of body 110 has, in its intermediate section, an axially extending male thread portion 119. The needle apparatus 115 is inserted in into member 110 with the flange or shoulder 118 coacting with the male thread 119 so that the hollow cylindrical portion 117 is fitted onto the bottom end of the hub 120 with the bore 121 therein in communication with the hollow needle 116. It should be understood that reference herein, and in the claims hereof, that when the needle is described as being "fixed" to the needle holder means, it is intended to be descriptive of both the Figure 4 and FIG. 7 arrangements.

FIG. 12 shows a needle guard 130 made of plastic or other suitable material having a hollow axially elongated configuration. Guard 130 is essentially an elongated cup closed at the bottom (as shown) and having an open top 129. Adjacent the top opening 129, the cup has a tapered surface 128 sized so as to fit snuggly within the bore 55" at the bottom 57 of the needle holder 55. The cup 130 has sufficient axial extent so that it can enclose the needle 70 when tapered surface 128 is within bore 55" so as to prevent accidental contact of the point 71 by an errant body part. The member 130 further has the function of facilitating the maintenance of sterile condition for the needle during the period between the production and the utilization of the device. Further, a plurality of shallow notches 131 are provided in outer surface of tapered surface 128 to facilitate the permeation of an appropriate gas, e.g., ethylene oxide, during sterilization of the syringe in general and needle in particular.

FIG. 15 shows the needle holder means 55 of FIG. 4 assembled with the barrel of FIG. 1. More specifically, the needle holder means 55 carrying the hollow needle means 70 is positioned within the bottom barrel portion 34 with the male threads 58 and the female threads 35' in mutual mating and coacting engagement and with the pointed end 71 of the needle means 70 projecting axially down below or beyond the bottom end 32 of the barrel member by the dimension BB. The apparatus as shown in FIG. 15 further includes the plunger assembly 95; all of the apparatus shown together with the needle guard 130 would be preassembled at a factory production facility. Apparatus for inserting the needle holder assembly 55 into barrel portion 34 is described in some detail below in connection with FIGS. 16 and 17.

The apparatus as shown in FIG. 15 may be used in the conventional ways for either withdrawing body fluids or for injecting fluids into the body. As shown reference numeral 140 designates fluid located between the bottom of piston 99 and the top axial end 56 of the needle holder assembly 55. The fluid 140 would be drawn into the barrel via needle 70 from a supply, not shown, in the well known manner through manipulation of the plunger assembly. Assuming that the plunger assembly 95 is moved axially downwardly, relative to the barrel 30, the fluid 140 will be forced through bore 67' and hollow needle 70 to the point 71.

Once the syringe, as depicted in FIG. 15, has been utilized to the full extent as determined by medical staff, then it is desired to render the syringe fully safe against accidental sticking of medical staff personnel or other personnel. Accordingly, the preferred practice would be to have the person, who had utilized the syringe for the aforementioned conventional utilization, then immediately take steps to render the syringe safe by pushing the plunger assembly 95 axially downwardly, as shown in FIG. 14, until the teeth or tool means 104 on the bottom part of the piston means 99 are in engagement with the corresponding teeth 81 on the top axial end of the needle holder means 55. As the teeth elements 104 of the plunger begin to engage with the teeth elements 81, the coacting beveled surfaces thereof will automatically align the plunger (rotate it about its longitudinal axis) so that the teeth 104 are in full mutual mating engagement with teeth 81 as aforesaid. Upon such engagement of the torque transmission means, then the knob 106 on plunger 95 is manually rotated several turns, the rotation (and torque) applied to the plunger 95 being transmitted through the teeth 104 to the teeth 81 and thence to the needle holder means 55 thereby causing relative rotation between the needle holder means 55 and the barrel portion 34, the rotation being permitted by the mutually mating threads 58 and 35'. The aforesaid relative rotation between 55 and 34 cause the needle holder means 55 to be moved upwardly (With respect to the barrel 34); this upward axial movement continues until the male threads 58 disengage from the female threads 35'; at this point, the flared or tapered surface 64 at the bottom axial end of needle holder means 55 is adjacent to and in mating engagement with the tapered surface 37 at the top axial end of the threaded portion or threaded section of barrel portion 35, all as is shown in FIGS. 14 and 14A. Further, it will be noted that the shoulder 65 on the needle holder means 55 is abutted against the shoulder 44 at the bottom of taper 41, i.e. the shoulder 44 acts as a lock in its coaction with shoulder 65 and prevents a subsequent reinsertion of the needle holder means 55 into the female threaded section of barrel portion 34. In addition, the coacting tapered surfaces 64 and 37 function as a bearing permitting unlimited rotation, but also prevent the needle holder means from moving axially up as shown in FIG. 14.

The aforementioned dimensions AA and BB ar also shown on FIG. 14 to illustrate that when the needle assembly is fully withdrawn up into the barrel of the syringe, the tip 71 of the needle 70 is axially withdrawn up inside of the barrel portion 34 and is spaced axially from the bottom surface 32 a sufficient amount so that no accidental contact with point 71 could occur by an errant body part. It will be understood by those skilled in the art that the dimensions AA and BB can be preselected in accordance with criteria in addition to the safety function provided by our unique syringe; the key factor is to have AA longer than BB so as to provide the desired safety clearance for tip 71 of the needle 70 as shown in FIG. 14.

The factory assembly operation (above mentioned) can be accomplished in a variety of procedures. One arrangement which we have found satisfactory is shown in FIGS. 16 and 17; a driver 201 especially fitted with a hub having teeth similar to teeth 104 (see FIG. 10) for matching with the teeth 81 on the top axial end 56 of the needle holder means 55. Another special fixture for the assembly process is a leader tube 210; it is a thin walled semiflexible tube of suitable material such as stainless steel which is used as a temporary fixture for facilitating the insertion of the bottom axial end of the needle assembly through the opening 37' and thence into engagement with the female threads of barrel portion 34. Thus, the outside diameter of leader tube 210 is selected so that it will expand the top opening 37' of the bottom barrel portion 34. The top end of the leader tube 210, as depicted in FIG. 16, has a plurality of axially extending slots 211 to permit some flexibility of the outer diameter of the leader tube 210 as the needle assembly is pushed down inside of leader tube 210. This is the arrangement shown in FIG. 17. Thereafter, the tool means 201 is pushed both in a downward axial direction and also rotated as symbolized by the rotational vector 220. As the flared end of the leader tube (abutting the shoulder 65 and surrounding flared surface 64) is pushed through opening 37', the material of the barrel 30 may, because of resiliency, yield temporarily. In this manner the needle assembly may, at the factory, be pushed beyond the shoulder 44 because the top of the leader tube surrounds the bottom portion of the needle assembly, i.e. flared surface 64 and bottom end 63 and thus provides a smooth transition to facilitate the aforesaid insertion of the needle assembly into the bottom portion 34 of the barrel. It will be understood that the aforementioned downward and rotational movement of the tool 201 or the driver 201 will move the needle assembly 55 downwardly to the point where the male threads 58 thereon will engage with the female threads 35' in the lower barrel portion 34. Thereafter continued rotation of driver 201 in the direction 220 will move the needle assembly 55 all the way into a fully engaged position, i.e. as shown in FIG. 15.

Figure 18:
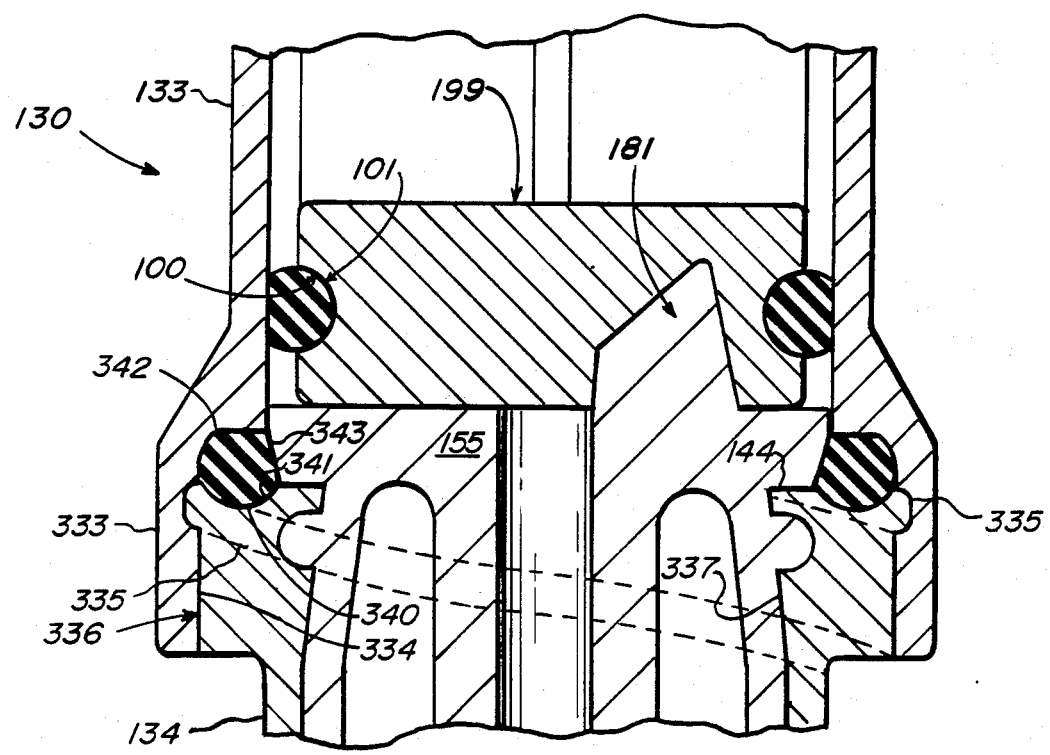
FIG. 18 shows, on a larger scale, a portion of a modified version of the invention characterized by the barrel member comprising separate top and bottom tubular portions detachably connected to one another.

FIG. 18 shows a modified syringe apparatus characterized by having the hollow barrel member comprised of separate detachable top and bottom tubular portions 133 and 134. As shown, the bottom end of top tubular portion 133 is of an enlarged outside diameter forming an attachment sleeve portion 333, the inner surface 334 of which is provided with a female threaded section 335, or other selected attachment means, for coaction with a complementary mating male threaded section 336 on the outside surface of the top end of bottom tubular portion 134.

The syringe of FIG. 18 further comprises a needle holder means 155 which may be essentially the same as either FIG. 4 or 7/7A, i.e. having (i) an external male threaded section adapted to coact with a female threaded section of the bottom tubular portion 134, and (ii) means 181 on the top axial end thereof for receiving the tool means on the bottom axial face of the plunger piston means 199 and for receiving torque from the plunger means (upon rotation thereof, as aforesaid) so that the needle holder means 155 is rotated relative to both our tubular portion 134 to thereby move axially upwardly into the top tubular portion 133. The automatic locking function, as aforesaid, is selectively available, if desired; tapered surface 337 and shoulder 144 being similar to elements 37 and 65 of the barrel 30 as best shown in FIG. 14A.

The apparatus of FIG. 18 is assembled by first preassembling elements 134 and 155; that subassembly is then coupled to the upper or top tubular barrel portion 133 using the attachment means 335/336. Preferably a liquid seal means is provided between elements 133 and 134; one arrangement is to have an "O" ring 340 captured between cooperating curved surfaces 341, 342 and 343 of elements 134, 133 and 155, respectively.

Although the embodiment of our invention shown in FIG. 18 is more complex than that of FIG. 14, it has certain advantages. First, and foremost, this arrangement permits having a family of bottom tubular barrel portions of different preselected axial lengths ranging from relatively short (for short needles) to relatively long (for long needles), said bottom barrel portions accommodating, respectively, a family of needle holder means of preselected axial lengths. Thus, if a short needle is desired, then dimension BB is short, and therefore a much shorted dimension AA can be used and still provide the "no-stick" function; the shorter AA dimension in turn permits a bottom barrel portion 134 of shorter axial extent. On the other extreme, if a very long needle is required, then a very long element 134 can be provided. Thus the FIG. 18 embodiment can facilitate a cost effective family of syringes covering all desired needle lengths. Another advantage of the FIG. 18 modification is a facilitating of automated assembly.

While we have described a preferred embodiment of the invention, it will be understood that the invention is limited only by the scope of the following claims.

We claim:
1. A safety syringe comprising:
(a) a cylindrical hollow barrel member having axially abutting and connected top and bottom tubular portions having, respectively, a top end and a bottom end, said bottom tubular portion having an internally disposed female threaded section of a preselected axial length, and said female threaded section having top and bottom axial ends;
(b) a cylindrical axially extended needle means having (i) top and bottom axial ends, (ii) an externally disposed male threaded section adjacent said bottom axial and of a preselected axial length and having top and bottom axial ends, and (iii) a central axially extending bore;
(c) elongated hollow needle means having a pointed end and being positioned in said central bore and fixed with respect to said needle holder means so that said pointed end of said hollow needle means projects a preselected axial extent beyond said bottom axial end of said needle holder means, said needle holder means being positioned within said barrel member bottom portion (i) with said male and female threaded sections in mutual mating and coacting engagement and said bottom axial end adjacent said bottom end of said barrel member, and (ii) so that said pointed end of said needle means is projecting axially beyond said bottom end of said barrel member;
(d) an elongated plunger means having a longitudinal axis and top and bottom ends and including (i) integral cylindrical piston means and (ii) torque transmitting tool means at said bottom end thereof insertable into said top portion of said barrel member so that, upon axial movement of said plunger means into said barrel member, said piston means and said tool means are moved axially toward and, after a preselected axial movement, said tool means is engageable with said top end of said needle holder means;

(e) means on said top end of said needle holder means for receiving said tool means and for receiving torque from said plunger means so that said needle holder means is thereby (i) rotated relative to said bottom tubular portion, and (ii) moved simultaneously axially upwardly in said bottom tubular portion toward said top axial end of said female threaded section; and (f) locking means for locking said needle holder means within said barrel member against any further axial movement, said locking means becoming effective automatically upon disengagement of said male threaded section from said female threaded section, whereby further use of said needle holder means is prevented, and said preselected axial length of said female threaded section of said bottom tubular portion of said barrel member being selected to be greater than said preselected axial projection of said hollow needle means beyond said bottom axial end of said needle holder means so that, upon said needle holder means being moved axially upwardly, said pointed end of said needle means is axially moved up into and within said bottom tubular portion of said barrel member and is axially displaced from said bottom end of said barrel member thus preventing accidental contact of said pointed end of said hollow needle means by an errant body part.

2. Apparatus of claim 1 further characterized by said locking means including coacting (i) means on said bottom axial end of said needle holder means and (ii) means on said top axial end of said female threaded section of said hollow barrel member.

3. Apparatus of claim 2 further characterized by said coacting means comprising:
(i) a circumferential groove on the exterior surface of said bottom axial end of said needle holder means immediately adjacent to said bottom axial end of said male threaded section, and
(ii) a reduced inner diameter of said hollow barrel member at said top axial end of said female threaded section.

4. Apparatus of claim 2 further characterized by said coacting means comprising:
(i) a skirt section immediately adjacent and flowing toward said bottom axial end of said needle holder means and a circumferential notch between said skirt section and the bottom axial end of said male thread section, and
(ii) a reduced inner diameter portion of said hollow barrel member at said top axial end of said female threaded section, whereby, upon disengagement of said male threaded section from said female threaded section, said reduced inner diameter portion of said hollow barrel member is disposed in said circumferential notch.

5. Apparatus of claim 1 further characterized by said torque transmitting tool means on said plunger means and said torque receiving means of said needle holder means including means for automatically rotationally aligning said plunger means with said needle holder means upon the aforesaid engagement of said tool means with said top end of said needle holder means.

6. A safety syringe comprising:
(a) a cylindrical hollow barrel member having axially abutting and connected top and bottom tubular portions having, respectively, a top end and a bottom end, said bottom tubular portion having an internally disposed female threaded portion of a preselected axial length;
(b) a cylindrical axially extended needle holder means having (i) top and bottom axial ends (ii) an externally disposed male threaded portion adjacent the bottom axial end of preselected axial length, and (iii) a central axially extending bore;
(c) elongated hollow needle means having a pointed end and being positioned in said central bore and fixed with respect to said needle holder means so that said pointed end of said hollow needle means projects a preselected axial extent beyond said bottom axial end of said needle holder means, said needle holder means being positioned within said barrel member bottom portion (i) with said male and female threaded portions in mutual engagement and said bottom axial end adjacent said bottom end of said barrel member, and (ii) so that said pointed end of said needle means is projecting axially beyond said bottom end of said barrel member;
(d) an elongated plunger means having top and bottom ends and including integral cylindrical piston means at said bottom end thereof insertable into said top portion of said barrel member so that, upon axial movement of said plunger means into said barrel member, said piston means is moved axially toward into engagement with said top end of said needle holder means; and
(e) torque transmitting tool means on said bottom end of said plunger means;
(f) means on said top end of said needle holder means for receiving said tool means and for transmitting torque from said plunger means to said needle holder means so that said needle holder means is (i) rotated relative to said barrel member, and (ii) moved simultaneously axially upwardly in said bottom tubular portion, said preselected axial length of said female threaded portion of said bottom tubular portion of said barrel member being selected to be greater than said preselected axial projection of said hollow needle means beyond said bottom axial end of said needle holder means so that, upon said needle holder means being moved axially upwardly, said pointed end of said needle means is axially moved up into said bottom tubular portion of said barrel member and is axially displaced from said bottom end of said barrel member thus preventing accidental contact of said pointed end of said hollow needle means by an errant body part.

7. Apparatus of claim 6 further characterized by said torque transmitting tool means on said plunger means and said torque receiving means on said needle holder means including means for automatically rotationally aligning said plunger means with said needle holder means upon the aforesaid engagement of said tool means with said top end of said needle holder means.

8. A safety syringe comprising:
(a) a cylindrical hollow barrel member having axially abutting and connected top and bottom tubular portions having, respectively, a top end and a bottom end, said bottom tubular portion having a top end and an internally disposed female threaded section having a top axial end;
(b) a cylindrical axially extended needle holder means having (i) top and bottom axial ends, (ii) an externally disposed male threaded section having a bottom axial end, and (iii) a central axially extending bore;

(c) elongated hollow needle means having a pointed end and being positioned in said central bore and fixed with respect to said needle holder means so that said pointed end of said hollow needle means projects beyond said bottom axial end of said needle holder means, said needle holder means being positioned within said barrel member bottom portion (i) with said male and female threaded sections in mutual mating and coacting engagement and said bottom axial end adjacent said bottom end of said barrel member, and (ii) so that said pointed end of said needed means is projecting axially beyond said bottom end of said barrel member;

(d) an elongated plunger means having a longitudinal axis and top and bottom ends and including (i) integral cylindrical piston means and (ii) torque transmitting tool means at said bottom end thereof insertable into said top portion of said barrel member so that, upon axial movement of said plunger means into said barrel member, said piston means and said tool means are moved axially toward and said tool means is engageable with said top end of said needle holder means;

(e) means on said top end of said needle holder means for receiving said tool means and for receiving torque from said plunger means about so that said needle holder means is thereby (i) rotated relative to said bottom tubular portion, and (ii) moved simultaneously axially upwardly in said bottom tubular portion toward said top axial end of said female threaded section; and (f) locking means for locking said needle holder means to said top end of said bottom tubular portion within said barrel member, said needle holder means being held by said locking means against any further axial movement relative to said barrel member upon disengagement of said male threaded section from said female threaded section, whereby further use of said needle holder means is prevented.

9. Apparatus of claim 8 further characterized by said locking means becoming effective automatically upon said disengagement.

10. Apparatus of claim 9 further characterized by said locking means including coacting (i) means on said bottom axial end of said needle holder means and means on said top axial end of said female threaded section of said hollow barrel member.

11. Apparatus of claim 10 further characterized by said coacting means comprising:
(i) a circumferential groove on the exterior surface of said bottom axial end of said needle holder means immediately adjacent to said bottom axial end of said male threaded section, and
(ii) a reduced inner diameter of said hollow barrel member at said top axial end of said female threaded section.

12. Apparatus of claim 10 further characterized by said coacting means comprising:
(i) skirt section immediately adjacent and flowing toward said bottom axial end of said needle holder means and a circumferential notch between said skirt section and the bottom axial end of said male thread section, and
(ii) a reduced inner diameter portion of said hollow barrel member at said top axial end of said female threaded section, whereby, upon disengagement of said male threaded section from said female threaded section, said reduced inner diameter portion of said hollow barrel member is disposed in said circumferential notch.

13. Apparatus of claim 8 further characterized by said torque transmitting tool means on said plunger means and said torque receiving means on said needle holder means including means for automatically rotationally aligning said plunger means with said needle holder means upon the aforesaid engagement of said tool means with said top end of said needle holder means.

14. A safety syringe comprising:
(a) a cylindrical hollow barrel member having axially abutting separate axially aligned top and bottom tubular portions having, respectively, a top end and a bottom end, said bottom tubular section having an internally disposed female threaded section of a preselected axial length, and said female threaded section having top and bottom axial ends, said separate top and bottom tubular portions including connection means for permitting selective mutual attachment and detachment of said top and bottom tubular portions;
(b) a cylindrical axially extended needle holder means having (i) top and bottom axial ends, (ii) an externally disposed male threaded section adjacent the bottom axial end of a preselected axial length and having top and bottom axial ends, and (iii) a central axially extending bore;
(c) elongated hollow needle means having a pointed end and being positioned in said central bore and fixed with respect to said needle holder means so that said pointed end of said hollow needle means projects a preselected axial extent beyond said bottom axial end of said needle holder means, said needle holder means being positioned within said barrel member bottom tubular portion (i) with said male and female threaded sections is mutual mating and coacting engagement and said bottom axial end adjacent said bottom end of said barrel member, and (ii) so that said pointed end of said needle means is projecting axially beyond said bottom end of said barrel member;
(d) an elongated plunger means having a longitudinal axis and top and bottom ends and including (i) integral cylindrical piston means and (ii) torque transmitting tool means at said bottom end thereof insertable into said top portion of said barrel member so that, upon axial movement of said plunger means into said barrel member, said piston means and said tool means are moved axially toward and, after a preselected axial movement, said tool means is engageable with said top end of said needle holder means;
(e) means on said top end of said needle holder means for receiving said tool means and for receiving torque from said plunger means so that said needle holder means is thereby (i) rotated relative to said bottom tubular portion, and (ii) moved simultaneously axially upwardly in said bottom tubular portion toward said top axial end of said female threaded section; and
(f) locking means for locking said needle holder means within said barrel member against any further axial movement, said locking means becoming effective automatically upon disengagement of said male threaded section from said female threaded section, whereby further use of said needle holder means is prevented, and said preselected axial length of said female threaded section of said bottom tubular portion of said barrel member being selected to be greater than said preselected axial projection of said hollow needle means beyond said bottom axial end of said needle holder means so that, upon said needle holder means being moved axially upwardly, said pointed end of said needle means is axially moved up into and within said bottom tubular portion of said barrel member and is axially displaced from said bottom end of said barrel member thus preventing accidental contact of said pointed end of said hollow needle means by an errant body part.

15. Apparatus of claim 14 further characterized by said locking means including coacting (i) means on said bottom axial end of said needle holder means and (ii) means of said top axial end of said female threaded section of said hollow barrel member.

16. Apparatus of claim 15 further characterized by said coacting means comprising:

(i) a circumferential groove on the exterior surface of said bottom axial end of said needle holder means immediately adjacent to said bottom axial end of said male threaded section, and (ii) a reduced inner diameter of said hollow barrel member at said top axial end of said female threaded section, whereby, upon disengagement of said male threaded section from said female threaded section, said reduced inner diameter of said hollow barrel member is disposed in said circumferential groove.

17. Apparatus of claim 14 further characterized by said connection means of said top and bottom tubular portions comprising male and female threaded means adapted to be selectively coupled in mutual mating and coacting engagement to thereby hold said top and bottom tubular portions in axially abutting and coaxial relationship.

18. Apparatus of claim 17 further characterized by means for sealing the connection of said top and bottom tubular portions and for sealing the connection of said needle holder means to said bottom tubular portion.

* * * * *